(12) United States Patent
Hamada

(10) Patent No.: US 7,083,680 B2
(45) Date of Patent: Aug. 1, 2006

(54) SUBLIMATION AND PURIFICATION METHOD

(75) Inventor: Yuji Hamada, Nara (JP)

(73) Assignee: Sanyo Electric Co., Ltd., Moriguchi (JP)

(*) Notice: Subject to any disclaimer, the term of this patent is extended or adjusted under 35 U.S.C. 154(b) by 632 days.

(21) Appl. No.: 10/252,013

(22) Filed: Sep. 23, 2002

(65) Prior Publication Data

US 2003/0089305 A1    May 15, 2003

(30) Foreign Application Priority Data

Sep. 25, 2001    (JP)    ............................. 2001-292499

(51) Int. Cl.
  *C30B 25/12*    (2006.01)
  *C30B 25/14*    (2006.01)

(52) U.S. Cl. .................. 117/104; 117/107; 117/109; 438/477; 438/502

(58) Field of Classification Search ................ 117/107, 117/109, 104; 438/477, 502; 423/508
See application file for complete search history.

(56) References Cited

U.S. PATENT DOCUMENTS

| 4,190,486 A | * | 2/1980 | Kyle | ........................ 438/502 |
| 4,507,160 A | * | 3/1985 | Beck et al. | .................. 438/477 |
| 4,613,495 A | * | 9/1986 | Gentile et al. | .............. 423/508 |
| 5,201,985 A | * | 4/1993 | Medvedieff | .................. 117/109 |

OTHER PUBLICATIONS

H.J. Wagner, et al., *Journal of Materials Science*, "Purification and characterization of phthalocyanines" vol. 17, pp. 2781-2791 (1982).

* cited by examiner

*Primary Examiner*—Felisa Hiteshew
(74) *Attorney, Agent, or Firm*—Armstrong, Kratz, Quintos, Hanson & Brooks, LLP

(57) ABSTRACT

A glass bottle containing a sample of an organic material to be purified is located at a position surrounded by a heater near one end in an outer glass tube. An inner glass tube for catching organic crystals obtained by recrystallization is located at a position near the other end in the outer glass tube. When the sample of the organic material is sublimed and purified, the inside of the outer glass tube is kept in a higher vacuum state (lower pressure) than 200 Pa by a vacuum pump. The sample inside the outer glass tube is heated by the heater, to sublime organic molecules of the sample contained in the glass bottle. The outer glass tube is provided with a temperature gradient, so that organic molecule vapor is cooled near the other end in the outer glass tube, and is recrystallized inside the inner glass tube.

14 Claims, 2 Drawing Sheets

SUBLIMATION AND PURIFICATION METHOD

BACKGROUND OF THE INVENTION

1. Field of the Invention

The present invention relates to a method for sublimating and purifying an organic material.

2. Description of the Related Art

Organic electroluminescent elements (hereinafter referred to as organic EL elements) have been expected as new self-emission type elements. The organic EL element has a stacked structure in which a carrier transport layer (an electron transport layer or a hole transport layer) and a luminescent layer are formed between a hole injection electrode and an electron injection electrode.

Organic materials are used for the hole transport layers, the luminescent layers, and the electron transport layers. Materials having the property of p-type semiconductors are used for the hole transport layers, and materials having the property of n-type semiconductors are used for the electron transport layers. The luminescent layers also have carrier transportability such as electron transportability or hole transportability, and are composed of organic materials for emitting fluorescence or phosphorescence.

The hole injection electrode, the hole transport layer, the luminescent layer, the electron transport layer, and the electron injection electrode are stacked in this order, thereby forming the organic EL element.

Examples of factors that affect the luminescent characteristics of the organic EL elements include the purity of organic materials. When impurities are contained in the organic materials, the impurities become traps for carriers and cause light extinction, resulting in reduced luminous intensity and luminous efficiency. In order to reduce the amounts of the impurities, therefore, the organic materials must be purified.

As methods of purifying organic materials, recrystallization using solvents and recrystallization by sublimation are generally used. In the recrystallization using solvents, the organic materials can be purified in large amounts. Because the solvents are used, however, the solvents are easily incorporated in organic crystals. The solvents incorporated in the organic crystals function as impurities, which may reduce luminescent characteristics.

On the other hand, in the recrystallization by sublimation, the organic materials are sublimed in the vapor under vacuum and are recrystallized, whereby the impurities are difficult to incorporate. Consequently, the use of sublimation and purification methods prevails for the purification of the organic materials for the organic EL elements.

An article by H. J. Wagner. et al., Journal of Materials Science, 17, 2781, (1982) describes a method of subliming and purifying an organic material. FIG. 3 is a schematic view showing the configuration of a main portion of a sublimation and purification apparatus used for the sublimation and purification method described in the article.

As shown in FIG. 3, a glass tube 1 having a length of approximately 1 m is inserted into a copper tube 2 for thermal conduction. A sample 100 of an organic material to be purified is located near one end in the glass tube 1. A heater 5 is mounted so as to surround the copper tube 2 around the sample 100 of the organic material.

The inside of the glass tube 1 is maintained in a vacuum state of approximately 200 Pa. The heater 5 heats the sample 100 in the glass tube 1, to sublime organic molecules of the sample 100. The glass tube 1 is provided with a temperature gradient, so that organic molecule vapor is cooled near the other end in the glass tube 1, and is recrystallized. Consequently, organic crystals 200 obtained by the recrystallization are formed near the other end in the glass tube 1. After the sublimation of the sample 100 is terminated, the glass tube 1 is broken using a gas burner, to take out the organic crystals 200. The organic material can be thus sublimated and purified.

However, the conventional method of sublimating and purifying an organic material described in the above-mentioned article involves work for breaking the glass tube 1 using the gas burner, whereby the work is complicated. Further, the glass tube 1 must be thrown away after the use, resulting in raised cost.

Furthermore, the organic crystals 200 are easily scattered in the glass tube 1. The organic material is difficult to sublime, and the purification yield thereof is low.

SUMMARY OF THE INVENTION

An object of the present invention is to provide a sublimation and purification method in which an organic material can be sublimed and purified simply and at low cost, and a high purification yield is obtained.

A method for subliming and purifying an organic material according to the present invention comprises the steps of inserting a collection tube for catching the organic material into a outer tube for sublimation; locating the organic material inside the outer tube; bringing the inside of the outer tube into a vacuum state; and heating the organic material located inside the outer tube to catch the sublimed organic material by the collection tube.

In the sublimation and purification method according to the present invention, the collection tube for catching the organic material is inserted into the outer tube for sublimation, and the organic material is located inside the outer tube. The inside of the outer tube is brought into the vacuum state, the organic material located inside the outer tube is heated to sublimate the organic material, and the sublimated organic material is caught by the collection tube inserted into the outer tube. Consequently, organic molecule vapor is cooled, thereby forming organic crystals obtained by recrystallization inside the collection tube.

After the sublimation and purification of the organic material are terminated, the collection tube is taken out of the outer tube for sublimation without breaking the outer tube. The organic crystals adhering to the inside of the collection tube are taken out. After the organic crystals are taken out of the collection tube, the outer tube and the collection tube are cleaned by the solvent. Consequently, the outer tube and the collection tube can be used many times.

The necessity of complicated work for breaking the outer tube in taking out the organic crystals obtained by the sublimation and purification is thus eliminated, whereby working time is short. Further, the outer tube and the collection tube can be repeatedly used, resulting in lowered cost.

Furthermore, the organic crystals are caught in the collection tube without being scattered inside the outer tube, resulting in increased purification yield.

The step of locating the organic material may include the step of inserting a container into the outer tube in a state where the organic material is contained therein.

In this case, the container is inserted into the outer tube in a state where the organic material is contained in the container, thereby making it possible to easily locate the organic material to be sublimed and purified at a predetermined position inside the outer tube. Further, the organic material to be sublimed and purified is prevented from being scattered inside the outer tube.

The step of inserting the container may include the step of inserting the container with its opening directed toward the collection tube.

In this case, the organic material sublimed inside the container is discharged from the opening on the side of the collection tube, and is efficiently caught in the collection tube. Consequently, the purification yield is further improved.

The step of inserting the container may include the step of inserting a glass bottle having an opening as the container into the outer tube.

In this case, the glass bottle is inserted into the outer tube in a state where the organic material is contained in the glass bottle, thereby making it possible to easily locate the organic material to be sublimed and purified at a predetermined position inside the outer tube. Further, the organic material to be sublimed and purified is prevented from being scattered inside the outer tube.

The step of heating the organic material may include the step of providing the outer tube with a temperature gradient such that a temperature at the position of the organic material located inside the outer tube is higher than a temperature at the position of the collection tube.

Consequently, organic molecule vapor from the sublimed organic material is satisfactorily cooled in the collection tube, thereby forming organic crystals obtained by recrystallization inside the collection tube.

The step of heating the organic material may include the step of providing a heater at a position outside the outer tube and facing to the organic material. Consequently, the organic material inside the outer tube can be easily heated.

The step of providing the heater may include the step of inserting the outer tube into a thermal conduction tube and providing the heater outside the thermal conduction tube. Consequently, the temperature inside the outer tube is maintained at a predetermined temperature.

The step of inserting the outer tube into the thermal conduction tube may include the step of inserting the outer tube into a metal tube as the thermal conduction tube. Since the metal tube has good heat conductivity, the temperature inside the outer tube is maintained at a predetermined temperature.

The step of bringing the inside of the outer tube into the vacuum state may include the step of making pressure inside the outer tube lower than 200 Pa. Consequently, the purification yield is further improved.

The step of bringing the inside of the outer tube into the vacuum state may include the step of connecting a vacuum gauge to one end, on the side of the organic material, of the outer tube and connecting a vacuum pump to the other end, on the side of the collection tube, of the outer tube. In this case, the organic material sublimed inside the outer tube is smoothly introduced toward the collection tube. Consequently, the purification yield is improved.

The step of locating the organic material inside the outer tube may include the step of locating the organic material near the one end in the outer tube, and the step of inserting the collection tube may include the step of locating the collection tube near the other end in the outer tube. In this case, the organic material is inserted from the one end of the outer tube, and the collection tube is inserted from the other end thereof, thereby making it possible to easily locate the organic material and the collection tube inside the outer tube.

The step of inserting the collection tube may include the step of locating in the outer tube a glass tube having a smaller outer diameter than the inner diameter of the outer tube as the collection tube. In this case, the collection tube can be repeatedly used.

The sublimation and purification method may further comprise the step of preparing a glass tube or a metal tube as the outer tube. Consequently, the outer tube can be repeatedly used.

The sublimation and purification method may further comprise the step of inserting the outer tube into a thermal insulating box. Consequently, the outer tube can be maintained at a predetermined temperature.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
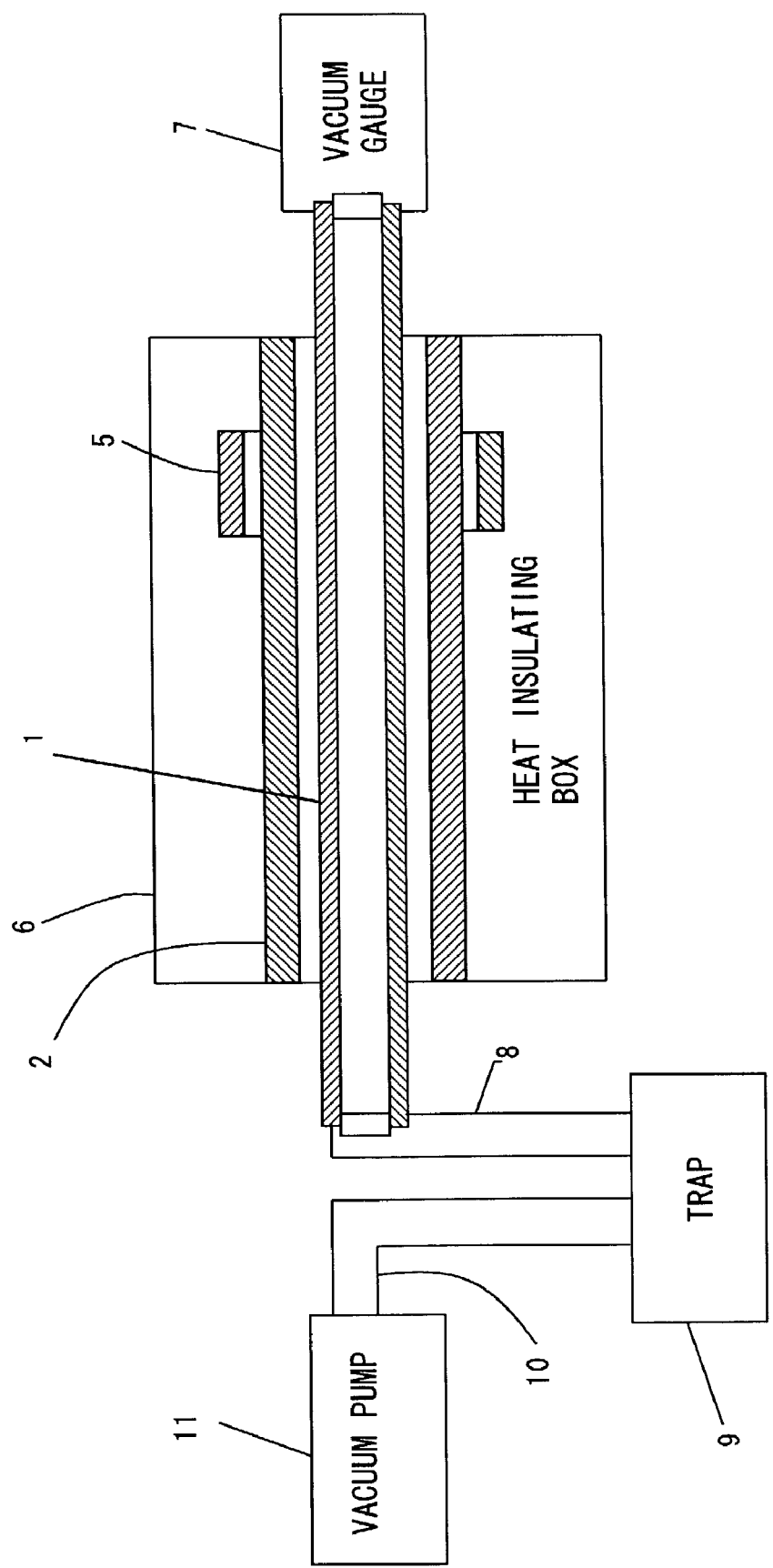
FIG. 1 is a schematic cross-sectional view showing the configuration of a sublimation and purification apparatus used for a sublimation and purification method in one embodiment of the present invention.
Figure 2:
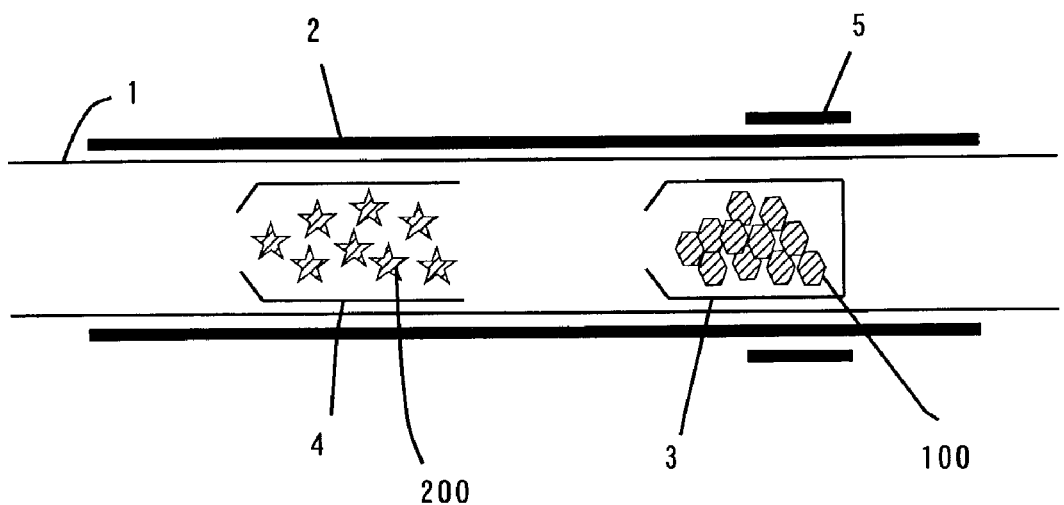
FIG. 2 is a schematic cross-sectional view of a main portion of the sublimation and purification apparatus shown in FIG. 1.

FIG. 1 is a schematic cross-sectional view showing the configuration of a sublimation and purification apparatus used for a sublimation and purification method in one embodiment of the present invention. FIG. 2 is a schematic cross-sectional view of a main portion of the sublimation and purification apparatus shown in FIG. 1.

As shown in FIG. 1, a copper tube 2 for thermal conduction is mounted in a thermal insulating box 6, and an outer glass tube 1 having a length of approximately 1 m is inserted into the copper tube 2. A heater 5 is mounted so as to surround the copper tube 2 near one end of the copper tube 2.

A vacuum gauge 7 is mounted on one end of the outer glass tube 1. A trap 9 is connected to the other end of the outer glass tube 1 through a pipe 8, and a vacuum pump 11 is connected to the trap 9 through a pipe 10.

As shown in FIG. 2, a glass bottle 3 containing a sample 100 of an organic material to be purified is located at a position surrounded by the heater 5 near the one end in the outer glass tube 1. An inner glass tube 4 for catching organic crystals obtained by recrystallization is inserted into a position near the other end in the outer glass tube 1. An opening of the glass bottle 3 is directed toward the inner glass tube 4.

When the sample 100 of the organic material is sublimed and purified, the inside of the outer glass tube 1 is kept in a higher vacuum state (lower pressure) than 200 Pa by the vacuum pump 11. The heater 5 heats the sample 100 inside the outer glass tube 1, to sublime organic molecules of the sample 100 contained in the glass bottle 3. The outer glass tube 1 is provided with a temperature gradient such that a temperature at the position of the glass bottle 3 is higher than a temperature at the position of the glass tube 4. Organic molecule vapor is cooled near the other end in the outer glass tube 1, is caught in the inner glass tube 4, and is recrystallized. Consequently, organic crystals 200 obtained by the recrystallization are formed inside the inner glass tube 4.

After the sublimation of the sample 100 is terminated, the inner glass tube 4 is taken out of the outer glass tube 1 without breaking the outer glass tube 1. The organic crystals 200 adhering to the inside of the inner glass tube 4 are taken out. After the organic crystals 200 are taken out of the inner glass tube 4, the inner glass tube 4 and the outer glass tube 1 are cleaned by a solvent. Consequently, the outer glass tube 1 and the inner glass tube can be used many times.

In the sublimation and purification method according to the present embodiment, the necessity of complicated work for breaking the outer glass tube 1 is eliminated, whereby working time is short. Further, the outer glass tube 1 and the inner glass tube 4 can be repeatedly used, resulting in reduced cost.

Furthermore, the organic crystals 200 are caught in the inner glass tube 4 without being scattered inside the outer glass tube 1, resulting in increased purification yield. The inside of the outer glass tube 1 is kept in a higher vacuum state than 200 Pa, so that the organic material is easily sublimed, and the purification yield thereof is further increased.

The outer glass tube 1 may be replaced with a tube made of a metal such as stainless steel. Further, the inner glass tube 4 may be replaced with a tube made of a metal such as stainless steel.

INVENTIVE EXAMPLE

Figure 3:
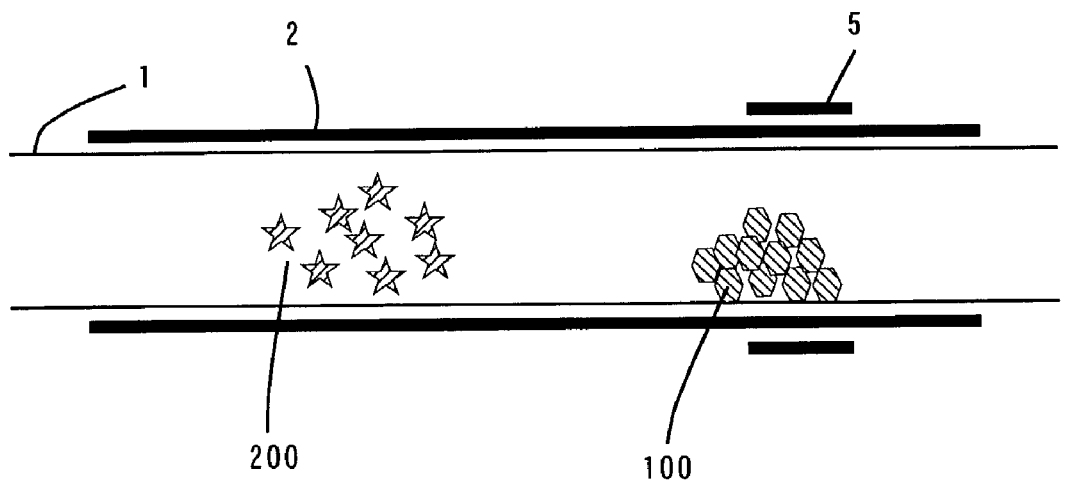
FIG. 3 is a schematic cross-sectional view of a main portion of a sublimation and purification apparatus used for a conventional sublimation and purification method.

In inventive examples 1 to 9, an organic material was sublimed and purified using the sublimation and purification apparatus shown in FIGS. 1 and 2. On the other hand, in comparative examples 1 and 2, an organic material was sublimed and purified using the sublimation and purification apparatus shown in FIG. 3.

In the inventive examples 1, 4, and 7 and the comparative example 1,N,N'-Di(naphthalen-1-yl)-N,N'-diphenyl-benzidine) (hereinafter referred to as NPB) having a molecular structure expressed by the following formula (1) was purified. In the inventive examples 2, 5, and 7 and the comparative example 2, tris(8-hydroxyquinolinato)aluminum (hereinafter referred to as Alq) expressed by the following formula (2) was purified. In the inventive examples 3, 6, and 9, Rubrene having a molecular structure expressed by the following formula (3) was purified.

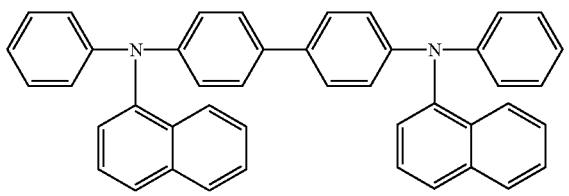

(1)

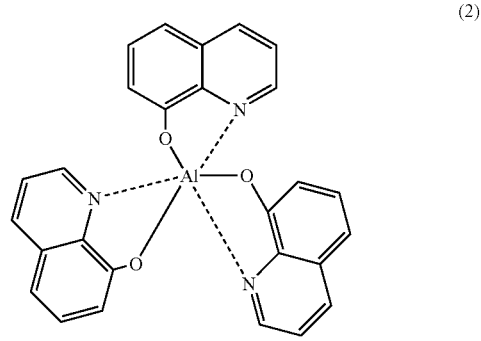

(2)

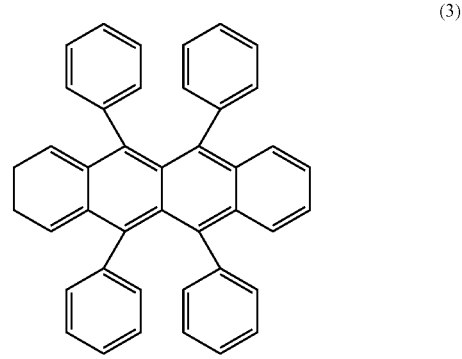

(3)

Table 1 shows the names of the organic materials and the amount of a prepared sample, the amount of recrystallization, the yield, the degree of vacuum, and the temperature corresponding to each of the organic materials in the inventive examples 1 to 9 and the comparative examples 1 and 2.

TABLE 1

|  | NAME OF MATERIAL | AMOUNT OF PREPARED SAMPLE (g) | AMOUNT OF RE-CRYSTALLIZATION (g) | YIELD (%) | DEGREE OF VACUUM (Pa) | TEMPERATURE (° C.) |
| --- | --- | --- | --- | --- | --- | --- |
| INVENTIVE EXAMPLE 1 | NPB | 1 | 0.91 | 91 | 12 | 280 |
| INVENTIVE EXAMPLE 2 | Alq | 1.5 | 0.56 | 32 | 12 | 280 |
| INVENTIVE EXAMPLE 3 | RUBRENE | 2.1 | 1.4 | 66 | 12 | 270 |
| INVENTIVE EXAMPLE 4 | NPB | 1 | 0.94 | 94 | $1.3 \times 10^{-2}$ | 280 |
| INVENTIVE EXAMPLE 5 | Alq | 1.5 | 0.71 | 47 | $1.3 \times 10^{-2}$ | 280 |
| INVENTIVE EXAMPLE 6 | RUBRENE | 2.1 | 1.6 | 77 | $1.3 \times 10^{-2}$ | 270 |
| INVENTIVE EXAMPLE 7 | NPB | 1 | 0.94 | 94 | $1.3 \times 10^{-4}$ | 280 |
| INVENTIVE EXAMPLE 8 | Alq | 1.5 | 0.9 | 60 | $1.3 \times 10^{-4}$ | 280 |

TABLE 1-continued

| | NAME OF MATERIAL | AMOUNT OF PREPARED SAMPLE (g) | AMOUNT OF RE-CRYSTALIZATION (g) | YIELD (%) | DEGREE OF VACUUM (Pa) | TEMPERATURE (° C.) |
|---|---|---|---|---|---|---|
| INVENTIVE EXAMPLE 9 | RUBRENE | 2.1 | 1.8 | 85 | $1.3 \times 10^{-4}$ | 270 |
| COMPARATIVE EXAMPLE 1 | NPB | 1.1 | 0.61 | 55 | 200 | 280 |
| COMPARATIVE EXAMPLE 2 | Alq | 1.5 | 0.12 | 8 | 200 | 280 |

In the inventive examples 1 to 3, purification was performed at a degree of vacuum of 12 Pa. In the examples 4 to 6, purification was performed at a degree of vacuum of $1.3 \times 10^{-2}$ Pa. In the inventive examples 7 to 9, purification was performed at a degree of vacuum of $1.3 \times 10^{-4}$ Pa.

In the inventive examples 1 to 9, the sample was contained in the glass bottle 3. As a result, it was possible to prevent the powdered sample from being scattered in starting to draw a vacuum inside the outer glass tube 1.

Furthermore, organic crystals obtained by recrystallization were caught in the inner glass tube 4. Accordingly, the inner glass tube 4 was taken out of the outer glass tube 1, thereby making it possible to take out the organic crystals without breaking the outer glass tube 1.

Both the outer glass tube 1 and the inner glass tube 4 were made usable many times by being cleaned using an organic solvent.

Comparison between the inventive examples 1, 4, and 7 and the comparative example 1 and comparison between the inventive examples 2, 5, and 8 and the comparative example 2 showed that the yield of Alq and Rubrene was improved as the degree of vacuum was increased.

On the other hand, with respect to the organic material with a yield of 90% or more at a degree of vacuum of 12 Pa, such as NPB, the yield was not improved even if the degree of vacuum was further increased. The reason for this was that the organic material was saturated with a yield of 90% or more. Further, when the organic material was sublimed at a degree of vacuum of 200 Pa, as in the comparative example 1, the yield was significantly reduced to 55%.

From the foregoing results, it is desirable that the organic material is sublimed and purified at a higher vacuum state than 200 Pa.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for subliming and purifying an organic material, comprising the steps of:
   inserting a collection tube for catching the organic material into an outer tube for sublimation;
   locating the organic material inside said outer tube;
   bringing the inside of said outer tube into a vacuum state; and
   heating the organic material located inside said outer tube to catch the sublimed organic material within said collection tube.

2. The method according to claim 1, wherein said step of locating the organic material includes the step of inserting a container into said outer tube in a state where the organic material is contained therein.

3. The method according to claim 2, wherein said step of inserting the container includes the step of inserting said container with its opening directed toward said collection tube.

4. The method according to claim 3, wherein said step of inserting the container includes the step of inserting a glass bottle having an opening as said container into said outer tube.

5. The method according to claim 1, wherein said step of heating the organic material includes the step of providing said outer tube with a temperature gradient such that a temperature at the position of the organic material located inside said outer tube is higher than a temperature at the position of said collection tube.

6. The method according to claim 1, wherein said step of heating the organic material includes the step of providing a heater at a position outside said outer tube and facing to the organic material.

7. The method according to claim 6, wherein said step of providing the heater includes the step of inserting said outer tube into a thermal conduction tube and providing said heater outside said thermal conduction tube.

8. The method according to claim 7, wherein said step of inserting the outer tube into the thermal conduction tube includes the step of inserting said outer tube into a metal tube as said thermal conduction tube.

9. The method according to claim 1, wherein said step of bringing the inside of the outer tube into the vacuum state includes the step of making pressure inside said outer tube lower than 200 Pa.

10. The method according to claim 1, wherein said step of bringing the inside of the outer tube into the vacuum state includes the step of connecting a vacuum gauge to one end, on the side of said organic material, of said outer tube and connecting a vacuum pump to the other end, on the side of said collection tube, of said outer tube.

11. The method according to claim 1, wherein said step of locating the organic material inside the outer tube includes the step of locating said organic material near the one end in said outer tube, and said step of inserting the collection tube includes the step of locating said collection tube near the other end in said outer tube.

12. The method according to claim 1, wherein said step of inserting the collection tube includes the step of locating in said outer tube a glass tube having a smaller outer diameter than the inner diameter of said outer tube as said collection tube.

13. The method according to claim 1, further comprises the step of preparing a glass tube or a metal tube as said outer tube.

14. The sublimation and purification method according to claim 1, further comprises the step of inserting said outer tube into a thermal insulating box.

* * * * *